(12) United States Patent  
Chen et al.

(10) Patent No.: US 9,417,105 B2
(45) Date of Patent: Aug. 16, 2016

(54) INTEGRATORS FOR SENSOR APPLICATIONS

(71) Applicant: AgaMatrix, Inc., Salem, NH (US)

(72) Inventors: Jun Chen, Warren, NJ (US); Igor Gofman, Croton-on-Hudson, NY (US); Mu Wu, Hopewell Jct., NY (US); Christopher Dionisio, Millington, NJ (US)

(73) Assignee: AgaMatrix, Inc., Salem, NH (US)

( * ) Notice: Subject to any disclaimer, the term of this patent is extended or adjusted under 35 U.S.C. 154(b) by 532 days.

(21) Appl. No.: 13/787,502

(22) Filed: Mar. 6, 2013

(65) Prior Publication Data

US 2014/0174145 A1 Jun. 26, 2014

Related U.S. Application Data

(60) Provisional application No. 61/745,178, filed on Dec. 21, 2012.

(51) Int. Cl.
| | |
|---|---|
| *G01D 18/00* | (2006.01) |
| *G01N 33/49* | (2006.01) |
| *A61B 5/145* | (2006.01) |
| *A61B 5/00* | (2006.01) |

(52) U.S. Cl.
CPC ............ *G01D 18/00* (2013.01); *A61B 5/14532* (2013.01); *A61B 5/7225* (2013.01); *G01N 33/49* (2013.01)

(58) Field of Classification Search
CPC .. A61B 5/7225; A61B 5/14532; A61B 5/145; A61B 2560/0276; A61B 5/14865; G01D 18/00; G01N 33/49
USPC ............... 702/22, 23; 600/345, 309, 365, 347
See application file for complete search history.

(56) References Cited

U.S. PATENT DOCUMENTS

| | | | | |
|---|---|---|---|---|
| 7,763,468 | B2 * | 7/2010 | Kawai | G01N 27/3273 422/68.1 |
| 8,323,195 | B2 * | 12/2012 | Ueda | A61B 5/14532 436/95 |
| 8,914,090 | B2 * | 12/2014 | Jain | A61B 5/0017 600/309 |
| 8,965,477 | B2 * | 2/2015 | Hoss | A61B 5/14532 600/345 |
| 2006/0241356 | A1 | 10/2006 | Flaherty | |
| 2007/0031971 | A1 * | 2/2007 | Kawai | G01N 27/3273 436/43 |
| 2009/0192751 | A1 | 7/2009 | Kamath et al. | |

(Continued)

FOREIGN PATENT DOCUMENTS

| | | |
|---|---|---|
| WO | 2009-042012 | 4/2009 |
| WO | 2010-109347 | 9/2010 |

*Primary Examiner* — Carol S Tsai
(74) *Attorney, Agent, or Firm* — Schwabe, Williamson & Wyatt, P.C.

(57) ABSTRACT

Embodiments herein provide processing of sensor signals (e.g., signals representative of a level of an analyte in a body). An electronics assembly may include a sensor contact configured to receive a sensor signal from a sensor assembly, an integrator circuit configured to provide an integrator output signal representative of the sensor signal integrated from a first time to a second time, and a reset circuit configured to reset the integrator output signal in response to a reset signal. The electronics assembly may also include a processor circuit configured to determine a value of the integrator output signal and to provide the reset signal to the reset circuit when an integration interval has elapsed from the first time. The integration interval may be based at least in part on the integrator output signal.

12 Claims, 10 Drawing Sheets

(56) References Cited

U.S. PATENT DOCUMENTS

| | | | |
|---|---|---|---|
| 2010/0099960 A1 | 4/2010 | Caduff et al. | |
| 2010/0317952 A1* | 12/2010 | Budiman | A61B 5/14532 600/365 |
| 2011/0257495 A1* | 10/2011 | Hoss | A61B 5/14532 600/347 |
| 2012/0078071 A1* | 3/2012 | Bohm | G06F 1/3203 600/345 |
| 2013/0018597 A1* | 1/2013 | Gofman | A61B 5/145 702/23 |
| 2014/0121477 A1* | 5/2014 | Jin | A61B 5/14532 600/301 |
| 2014/0121488 A1* | 5/2014 | Budiman | A61B 5/14532 600/365 |
| 2014/0148665 A1* | 5/2014 | Bernstein | A61B 5/14532 600/345 |
| 2014/0323960 A1* | 10/2014 | Sloan | A61B 5/0002 604/66 |

* cited by examiner

INTEGRATORS FOR SENSOR APPLICATIONS

CROSS-REFERENCE TO RELATED APPLICATION

This application claims priority to U.S. Provisional Application No. 61/745,178, titled "Integrators for Sensor Applications," filed Dec. 21, 2012, which is hereby incorporated by reference in its entirety herein.

TECHNICAL FIELD

Embodiments herein relate to the field of sensors, and, more specifically, to the processing of sensor signals.

BACKGROUND

Many medical sensors, such as continuous glucose monitoring (CGM) sensors include transimpedance amplifier circuitry for amplifying a sensor current signal. Such sensors often include a high resolution analog-to-digital converter (ADC) to further process the amplified signal. However, high resolution ADCs are typically more expensive and more energy intensive than lower resolution ADCs. Additionally, such sensors typically have low voltage-per-level and voltage-to-current ratios, and thus often exhibit undesirable sensitivity to electrical noise.

As an example, in order for existing glucose monitoring systems to achieve the minimum typically desired resolution of 5 picoamperes/level and cover the full range of current magnitudes produced by a CGM sensor (which, for illustrative purposes, may be approximately 5 microamperes), an ADC with a dynamic range of (5 microamperes)/(5 picoamperes/level)=1,000,000 levels is needed, corresponding to a 20-bit ADC ($2^{20}$=1,048,576). The transimpedance amplifier circuitry typically included in such systems often has a maximum output voltage of approximately 3 volts. The voltage-to-level ratio of such a system is then (3 volts)/(1,048,576 levels)=2.9 microvolts/level. Additionally, the value of the feedback resistor included in a transimpedance amplifier is typically selected so that the maximum range of voltage outputs are achieved: for a maximum output voltage of 3 volts and a maximum current of 5 microamperes, the value of the feedback resistor is typically selected to be as close as possible to (3 volts)/(5 microamperes)=600 kiloohms. Assuming that the typical operating range of sensor current is 1 picoampere (much lower than the initial 5 microampere value), the voltage-to-current ratio under typical operation is (1 picoampere)×(600 kiloohms)=0.6 microvolts/picoampere. For systems with voltage-to-level and voltage-to-current ratios this low, special hardware requirements are typically imposed and expensive components are typically used to protect sensitive circuitry from electrical noise.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

DETAILED DESCRIPTION

Figure 1:
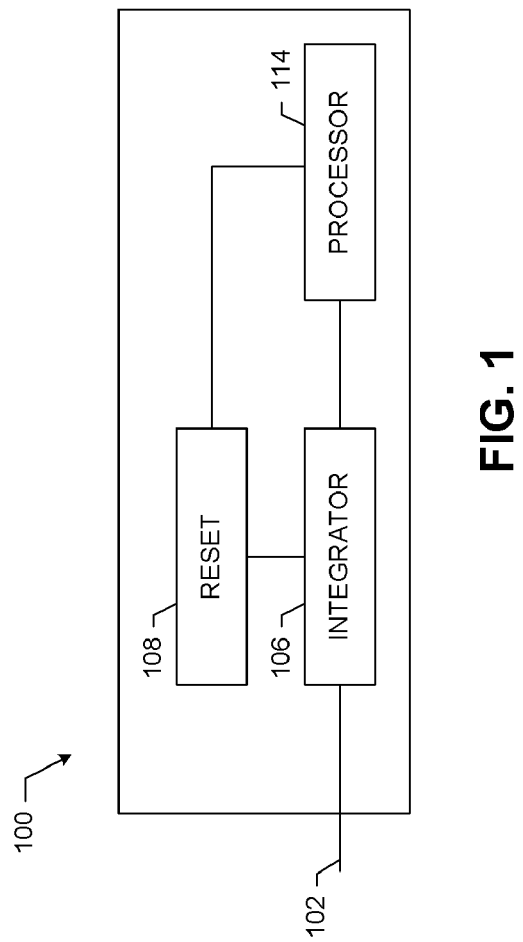
FIG. 1 is a block diagram of an electronics assembly including an integrator circuit and a reset circuit, in accordance with various aspects.

In the following detailed description, reference is made to the accompanying drawings which form a part hereof, and in which are shown by way of illustration embodiments that may be practiced. It is to be understood that other aspects and/or embodiments may be utilized and structural or logical changes may be made without departing from the scope. Therefore, the following detailed description is not to be taken in a limiting sense, and the scope is defined by the appended claims and their equivalents.

Various operations may be described as multiple discrete operations in turn, in a manner that may be helpful in understanding the disclosure; however, the order of description should not be construed to imply that these operations are order dependent.

The description may use perspective-based descriptions such as up/down, back/front, and top/bottom. Such descriptions are merely used to facilitate the discussion and are not intended to restrict the application of the disclosure.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. The term "aspect" generally refers to features or parts/components of disclosed embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Methods, apparatuses, and systems for processing sensor signals are provided. A computing device may be endowed with one or more components of the disclosed apparatuses and/or systems and may be employed to perform one or more methods as disclosed herein. The embodiments described herein may provide an alternative to traditional transimpedance amplifier/high resolution ADC sensors with any of a number of advantages, including lower cost, lower power consumption, better noise immunity, or a combination of the foregoing.

Various aspects are described in the context of a continuous glucose monitoring (CGM) sensor and/or system, although other types of sensors may use the signal processing methods, apparatuses and systems described herein. For example, the signal processing methods, apparatuses and systems described herein may be used with an electrochemical blood glucose monitoring (BGM) sensor and/or system (e.g., during intervals in which the BGM system measures an electrochemical property of a blood sample). The signal processing methods, apparatuses and systems described herein may be used with an optical blood glucose monitoring sensor and/or system (e.g., during intervals in which the optical blood glucose monitoring system measures an optical property of a patient's analyte using optical sensors, such as, but not limited to, PIN diodes. In some embodiments, the signal processing methods, apparatuses and systems described herein may be applied to an analog signal generated by an electrochemical BGM sensor and/or system, and/or an optical blood glucose monitoring sensor and/or system.

FIG. 1 is a block diagram of an electronics assembly 100 including an integrator circuit 106 coupled to a reset circuit 108, in accordance with various aspects. Integrator circuit 106 is coupled to a sensor contact 102 that is configured to receive a sensor signal from a sensor assembly. In some embodiments, the sensor signal provided by the sensor assembly is representative of a level of analyte in a body. For example, the sensor assembly may include a continuous glucose monitor (CGM) configured to produce the sensor signal. In some embodiments, integrator circuit 106 is configured to provide an integrator output signal representative of the sensor signal integrated from a first time to a second time. For example, the relationship between a sensor current signal Sensor(t) and an integrator output voltage signal Out(t) for the configuration of FIG. 1 may be given approximately by $$\text{Out(time2)} = \int_{time1}^{time2} (\alpha(t)\text{Sensor}(t) + \beta(t))dt, \quad (1)$$

where $\alpha$ and $\beta$ are constant or time-varying values. In some embodiments, time1 may be considered to be the origin of the time axis, in which case time1=0. In some embodiments, a constant or additional time-varying term may be added to Eq. 1 (e.g., to accommodate a non-zero time1 or to address or other constant or time-varying characteristics of electronics assembly 100).

Figure 2:
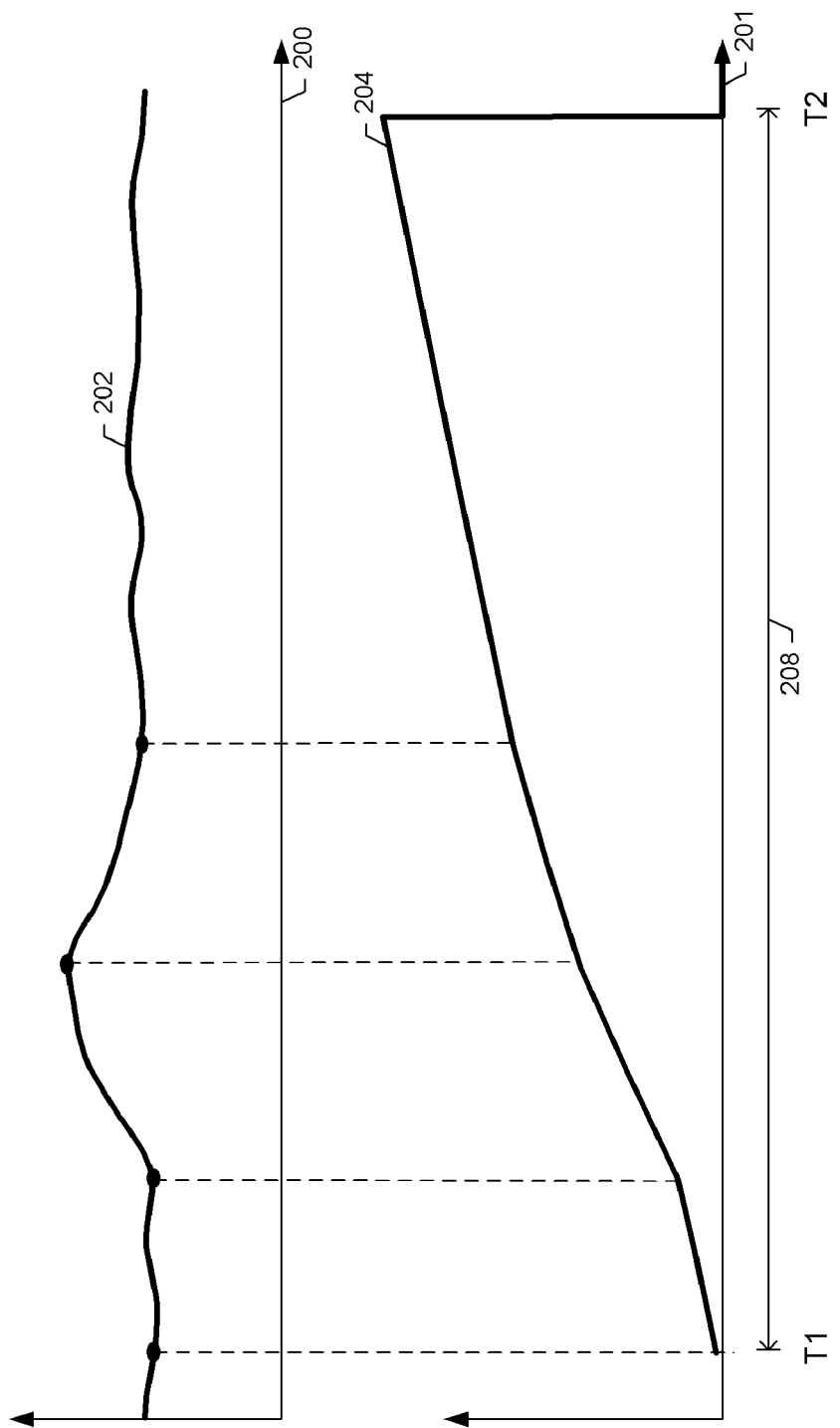
FIG. 2 illustrates an example sensor signal and corresponding integrator output signal that may be generated by an electronics assembly, such as the electronics assembly of FIG. 1, in accordance with various aspects.

FIG. 2 illustrates an example sensor signal 202 and corresponding integrator output signal 204 that may be generated by an electronics assembly, such as electronics assembly 100 of FIG. 1. Sensor signal 202 and integrator output signal 204 may be different types of signals; for example, sensor signal 202 may be a current signal and integrator output signal 204 may be a voltage signal. As shown, integrator output signal 204 is representative of sensor signal 202 integrated over an integration interval 208 from a first time T1 to a second time T2. Additionally, electronics assembly 100 may advantageously provide improved noise immunity due to the low pass filter effect of integrator circuit 106. In general, integration time may be adjusted to achieve a desired resolution and noise immunity.

Returning to FIG. 1, integrator circuit 106 is also coupled to a processor circuit 114. In some embodiments, processor circuit 114 is configured to determine a value of the integrator output signal provided by integrator circuit 106. Processor circuit 114 may determine this value in any of a number of ways, such as by measuring a value of the integrator output signal (e.g., as discussed below with reference to FIGS. 4-6) or by determining an elapsed time during which the integrator output signal rose to a threshold value (e.g., as discussed below with reference to FIGS. 7-9).

Processor circuit 114 is also coupled to reset circuit 108. Processor circuit 114 may include a processor (e.g., one or more microcontrollers) and supporting circuitry (e.g., wireless or wired communications circuitry). In some embodiments, processor circuit 114 is configured to provide a reset signal to reset circuit 108. In some embodiments, in response to receiving a reset signal from processor circuit 114, reset circuit 108 is configured to reset the integrator output signal provided by integrator circuit 106. As used herein, "resetting the integrator output signal" may refer to causing the integrator output signal to have a predetermined zero or non-zero value. Reset circuit 108 may continue to maintain the integrator output signal at the reset value until, for example, the reset signal is no longer received or an integration-initiation signal is received. As used herein, the term "stage" may refer to the period between separate integration initiation times. For example, a stage may begin when integrator circuit 106 initiates integration from a reset value (e.g., in response to no longer receiving a reset signal), continue through the receiving of a reset signal, and end when integrator circuit 106 again initiates integration from the reset value (at which point a next stage may begin).

In some embodiments, processor circuit 114 provides a reset signal to reset circuit 108 when an integration interval has elapsed from the first time T1. Upon receiving the reset signal, integrator circuit 106 may continue to integrate the sensor signal received at sensor contact 102 and provide a representative integrator output signal. For example, as illustrated in FIG. 2, integrator output signal 204 (plotted against time axis 201) represents sensor signal 202 (plotted against time axis 200) integrated over the integration interval 208 until a reset signal is received at second time 2T2, at which point the value of integrator output signal 204 resets to zero. In some embodiments, the integration interval is based at least in part on the integrator output signal. A number of examples of such embodiments are described herein.

Figure 3:
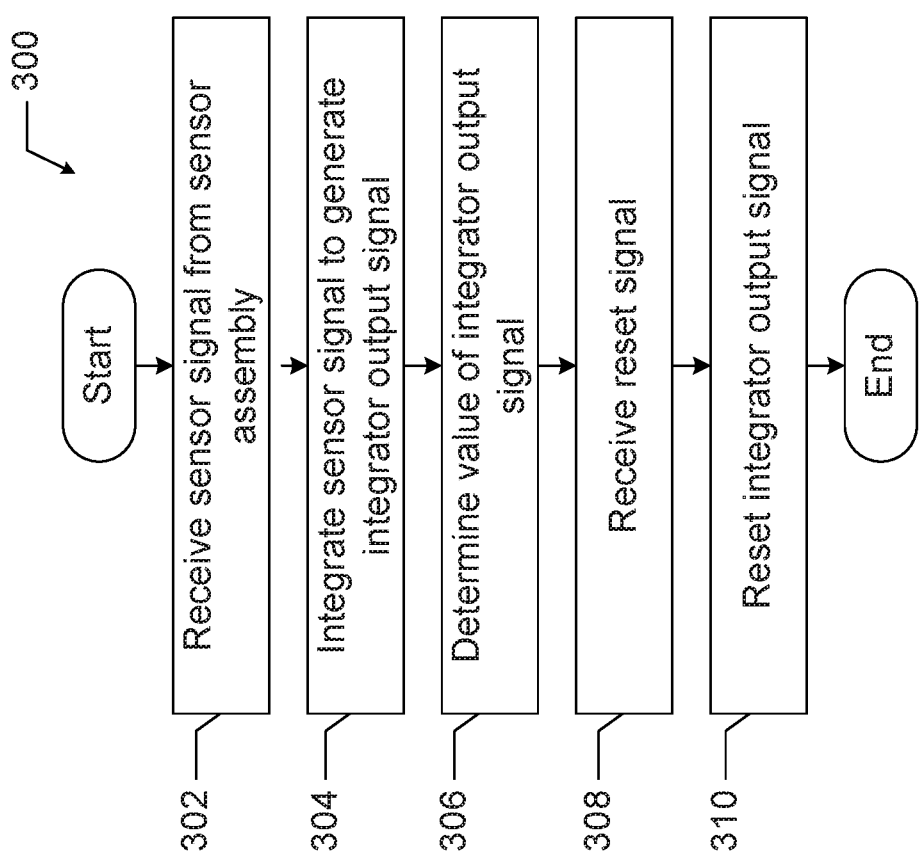
FIG. 3 is a flow diagram of a method of processing a sensor signal, which may use an electronics assembly such as the electronics assembly of FIG. 1, in accordance with various aspects.

FIG. 3 is a flow diagram 300 of a method of processing a sensor signal, which may use an electronics assembly such as electronics assembly 100 of FIG. 1, in accordance with various aspects. For ease of illustration, flow diagram 300 will be described as performed by electronics assembly 100, but the method of flow diagram 300 may be performed by any suitably configured apparatus (such as a programmed processing device or application specific integrated circuit). In some embodiments, the method of flow diagram 300 is performed at each stage of operation of an electronics assembly.

At block 302, electronics assembly 100 receives a sensor signal from a sensor assembly (e.g., via sensor contact 102 of FIG. 1). At block 304, electronics assembly 100 integrates the sensor signal from a first time to a second time to generate an integrator output signal. At block 306, electronics assembly 100 determines a value of the integrator input signal. In some embodiments, determining the value of the integrator output signal at block 306 includes measuring the value of the integrator output signal. At block 308, electronics assembly 100 receives a reset signal when an integration interval has elapsed from the first time. In some embodiments, the integration interval is based at least in part on the integrator output signal. At block 310, in response to receiving the reset signal at block 308, electronics assembly 100 resets the integrated output signal.

Figure 4:
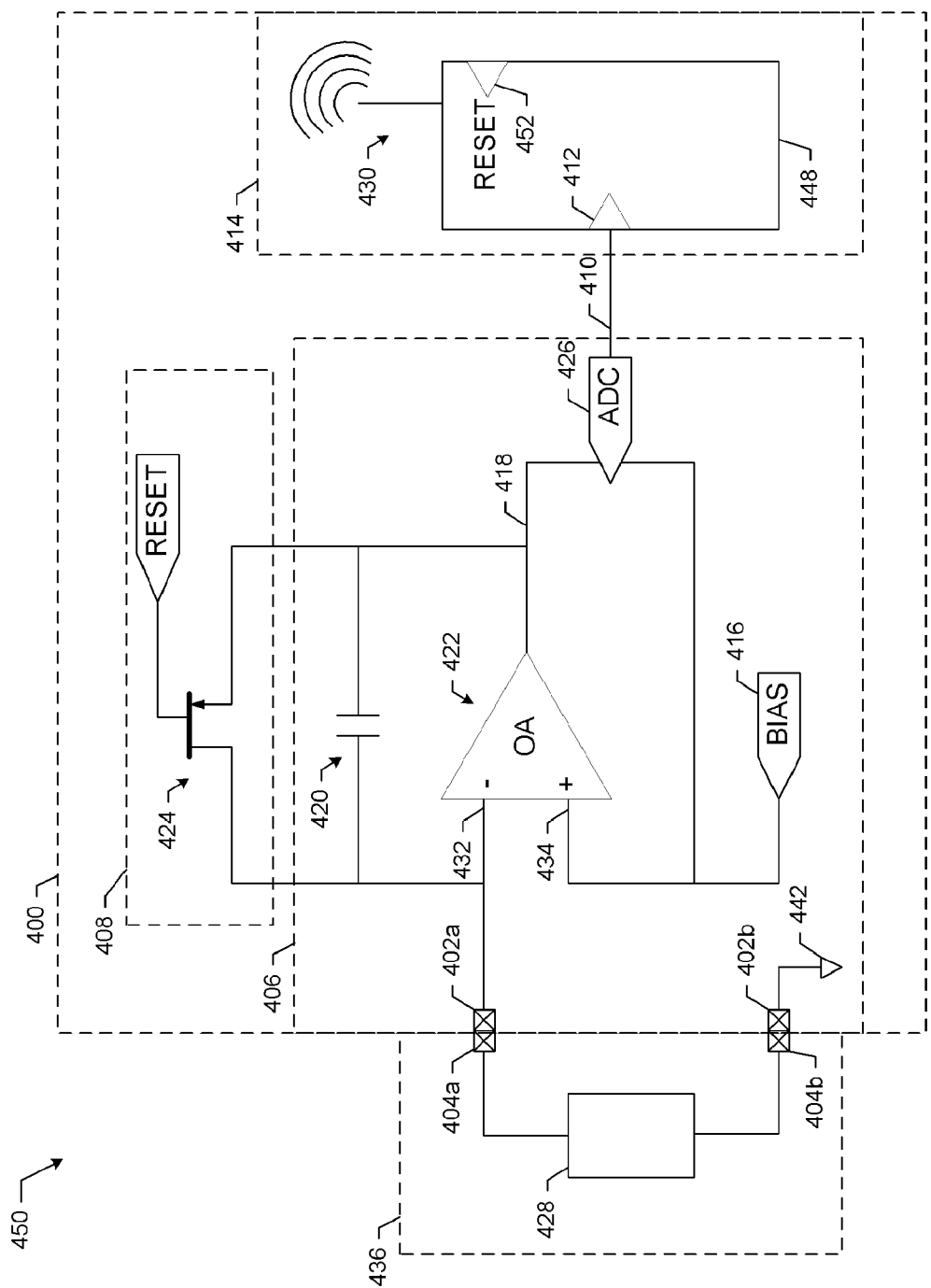
FIG. 4 is a schematic diagram of a sensor assembly and an electronics assembly including an analog-to-digital converter (ADC), in accordance with various aspects.

A number of embodiments of electronics assembly 100 of FIG. 1 are now described. FIG. 4 is a schematic diagram of a sensor system 450 including a sensor assembly 436 and an electronics assembly 400, in accordance with various aspects. Electronics assembly 400 may be an embodiment of electronics assembly 100 of FIG. 1, and may be configured to perform the signal processing method of FIG. 3, as discussed above.

As shown in FIG. 4, sensor assembly 436 includes a CGM sensor 428. In other embodiments, sensor 428 may be another type of biological sensor, such as, but not limited to, an optical sensor. Electronics assembly 400 includes an integrator circuit 406 (which may act as, e.g., integrator circuit 106 of FIG. 1) with an analog-to-digital converter (ADC) 426, and a processor circuit 414 (which may act as, e.g., processor circuit 114 of FIG. 1). The components of electronics assembly 400 may be packaged in a hermetic housing (not shown) that is configured to be releasably coupled to the sensor assembly 436.

Electronics assembly 400 includes sensor contacts 402a and 402b (which may act as, e.g., sensor contact 102 of FIG. 1) communicatively coupled with sensor contacts 404a and 404b of sensor assembly 436. As shown, contacts 402b and 404b are coupled to a ground potential 442.

Some embodiments of sensor system 450 including the CGM sensor 428 use a current measurement method. The current measurement method is based on the glucose oxidase enzymatic reaction, which converts glucose into gluconic acid and produces hydrogen peroxide. The hydrogen peroxide liberates electrons at the contact of a polarized electrode (not shown) of the CGM sensor 428. The enzyme is enclosed in a membrane that is selective for certain blood substrates and/or reaction products. The electrode detects an electrical current (i.e., the sensor signal), which is output to the electronics assembly at sensor contacts 404a and 404b. The sensor signal is converted into a glucose concentration by the processor circuit 414, which includes processor 448 and supporting circuitry (not shown).

When a CGM sensor, such as CGM sensor 428, is first attached to a body, the magnitude of the sensor signal typically begins in a high range (e.g., in the microamperes range) and decreases to a lower range for typical operation (e.g., in the nanoamperes to sub-nanoamperes range after several hours of use). An illustration of an example CGM sensor signal 502 is given in FIG. 5, which shows the initial high magnitude current values following initial sensor insertion around points 504a, and lower magnitude current values approaching a typical operating range around points 504b.

Returning to FIG. 4, electronics assembly 400 includes an integrator circuit 406. As shown, integrator circuit 406 is configured in a transimpedance integration configuration. In particular, the integrator circuit 406 includes an operational amplifier (OA) 422 and a capacitor 420 coupled between an input terminal 432 and an output terminal 418 of the OA 422. The input terminal 432 of OA 422 is coupled to the sensor contact 402a to receive the sensor signal from the CGM sensor 428. Integrator circuit 406 is biased with a bias voltage 416 to provide a bias for the CGM sensor 428. Accordingly, the voltage at the OA input terminal 432 is substantially equal to the bias voltage 416 at the OA input terminal 434 plus/minus an offset voltage of the OA 422. For an "ideal" OA 422, the offset voltage may be zero. The integrator circuit 406 receives the sensor signal from sensor contacts 402a at OA input terminal 432 and converts the OA input signal into an OA output signal at OA output terminal 418. In some embodiments, the relationship between a sensor current signal Sensor(t) and an OA output voltage signal Out(t) for the configuration of FIG. 4 may be given approximately by $$\text{Out}(time2) = \frac{1}{C} \int_{time1}^{time2} \text{Sensor}(t) dt, \quad (2)$$

where C is the capacitance of capacitor 420. If the average value of the sensor current signal Sensor(t) over the interval between time1 and time2 is represented by $I_S$, and the integration interval between time1 and time2 is represented by T, Eq. 2 may be written as $$\text{Out}(time2) = \frac{I_S \times T}{C} \quad (3)$$

In some embodiments, time1 may be considered to be the origin of the time axis, in which case time1=0. In such embodiments, when the integration interval has duration T, time2 is equal to T and thus Eq. 3 may be written as:

$$\text{Out}(T) = \frac{I_S \times T}{C}. \quad (4)$$

Thus, per Eqs. 3 and 4, the OA output signal has a voltage dependent on the current of the OA input signal; in particular, the slope of the OA output signal is proportional to the average value of the sensor current signal $I_S$. As shown in FIG. 4, the OA output signal at OA output terminal 418 is sent to ADC 426, which digitizes the OA output signal and passes the digital signal to processor circuit 414 via integrator output 410. In some embodiments, ADC 426 has a lower resolution than ADCs typically used in transimpedance amplifier-based sensor systems (e.g., a resolution of 18 bits or less). In some embodiments, a voltage amplifier (not shown) is coupled between OA output terminal 418 and ADC 426 to adjust the amplitude of the OA output signal before it is processed by ADC 426.

Electronics assembly 400 also has a reset circuit 408 (which may act as, e.g., reset circuit 108 of FIG. 1), which includes a FET 424 connected between OA input terminal 432 and OA output terminal 418 (and thereby in parallel with capacitor 420). Reset circuit 408 is configured to close FET 424 in response to receiving a reset signal from processor circuit 414 (via reset output 452), resetting integrator circuit 406 by shorting capacitor 420 of integrator circuit 406 and driving the value of the integrator output signal at integrator output 410 to zero. In some embodiments, reset circuit 408 includes other switch circuitry instead of or in addition to FET 424.

In some embodiments, some or all of the components of and around reset circuit 408 (which may include FET 424, capacitor 420 and OA 422) may be selected to have low leakage currents during use. When the leakage current of one or more of these components becomes large enough to interfere substantially with the signals in the circuitry (e.g., the integrator output signal at integrator output 410), the signals become more difficult to distinguish from the leakage current "noise." Additionally, the leakage current of various components may vary by environmental conditions such as temperature, and thus may introduce variations into the signal that are difficult to predict and control. In some embodiments, OA 422 may be selected from commercially available operational amplifiers that have a leakage current on the order of femtoamperes. In some embodiments, capacitor 420 may be selected from commercially available capacitors that have a leakage current on the order of femtoamperes. For example, in some embodiments, capacitor 420 may be a suitable polystyrene capacitor. In some embodiments, some or all of FET 424, capacitor 420 and OA 422 may be selected so that the magnitude of the total leakage current is less than approximately ten percent of the desired resolution of the integrator output signal. In some embodiments, some or all of FET 424, capacitor 420 and OA 422 may be selected so that the magnitude of the total leakage current is less than approximately five percent of the desired resolution of the integrator output signal. In some embodiments, some or all of FET 424, capacitor 420 and OA 422 may be selected so that the magnitude of the total leakage current is less than approximately one percent of the desired resolution of the integrator output signal.

As discussed above with reference to FIG. 1, in some embodiments, processor circuit 414 is configured to determine a value of the integrator output signal (received at input 412 of processor 448 via integrator output 410). Processor circuit 414 may also be configured to provide a reset signal to reset circuit 408 when an integration interval has elapsed. In some embodiments, processor circuit 414 is further configured to determine the integration interval based at least in part on a measurement of the integrator output signal. In some embodiments, the integrator output signal is reset each time a measurement of a value of the integrator output signal has been completed. Processor circuit 414 may further include an antenna 430 and other wireless communication circuitry (not shown) to convey data about the processed sensor signal to other computing devices (not shown).

In some embodiments, a measurement of the integrator output signal is taken before integrator circuit 406 saturates. The integration interval may also be adjusted to avoid saturation. For example, if the maximum output voltage of OA 422 is 3 volts and the capacitance of capacitor 420 is 50 nanofarads, the maximum integration time allowable when the sensor signal has an average current of 5 microamperes (according to Eq. 3) is (50 nanofarads)×(3 volts)/(5 microamperes)=30 milliseconds. Using the same circuit, the maximum integration time allowable when the sensor signal has an average current of 5 nanoamperes (according to Eq. 3) is (50 nanofarads)×(3 volts)/(5 nanoamperes)=30 seconds. Therefore, in some such embodiments, the interval between two consecutive reset signals may vary from 30 milliseconds to 30 seconds. When sensor system 450 first begins operation and the magnitude of the sensor signal is not known, the integration interval may be set to a sufficiently low value that integrator circuit 406 will not saturate even if the magnitude of the sensor signal is at its highest possible value (e.g., 1 second).

Figure 5:
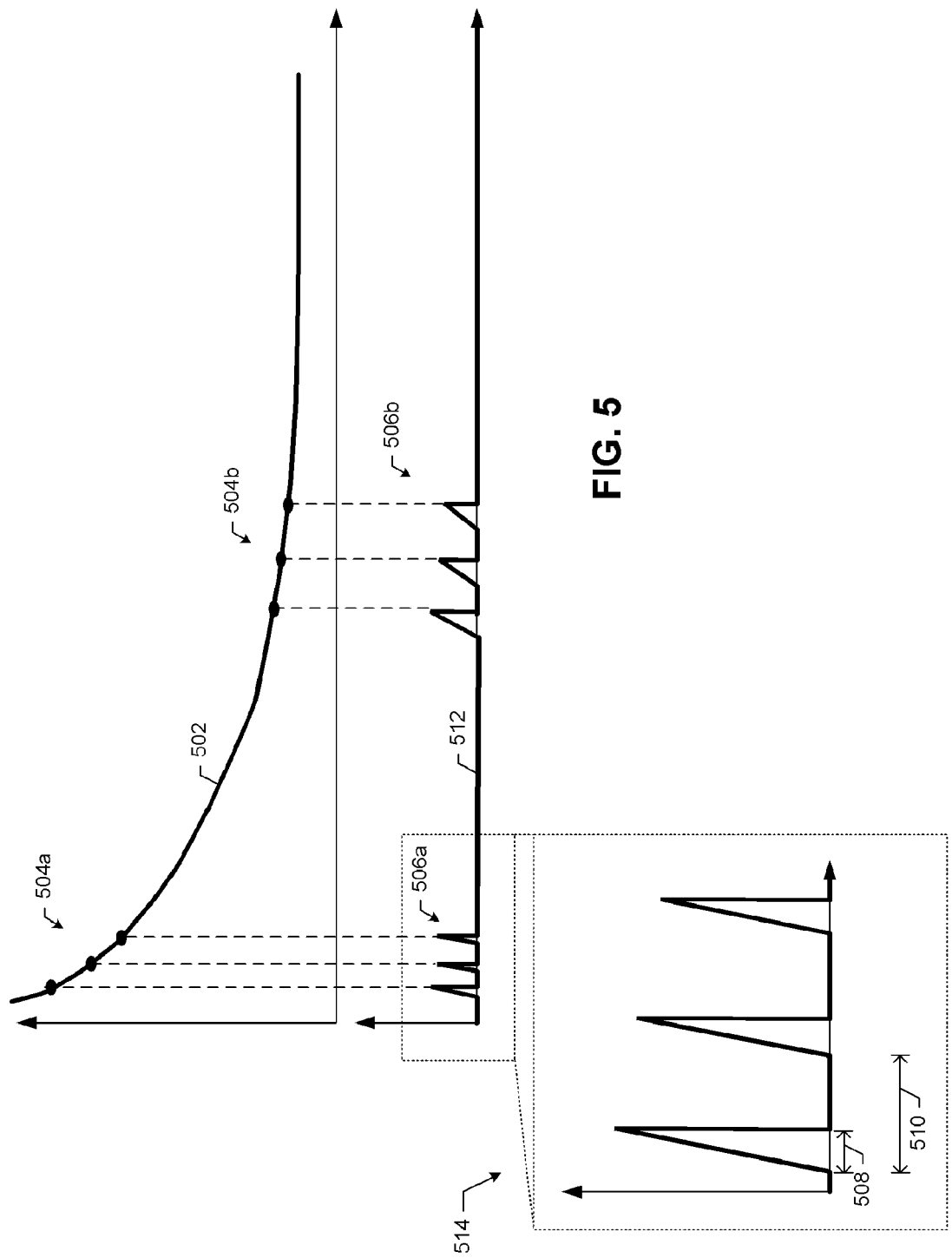
FIG. 5 illustrates an example sensor signal and corresponding integrator output signal that may be generated by an electronics assembly, such as the electronics assembly of FIG. 4, in accordance with various aspects.

To illustrate the operation of sensor system 450 of FIG. 4, FIG. 5 illustrates an example sensor signal 502 (that may be generated by, e.g., sensor assembly 436) and a corresponding integrator output signal 512 (that may be generated by, e.g., electronics assembly 400 of FIG. 4). As shown, integrator output signal 512 includes two collections of nonzero values: peaks 506a corresponding to points 504a of sensor signal 502 and peaks 506b corresponding to points 504b of sensor signal 502. These peaks 506a and 506b correspond to integration intervals (i.e., the periods during which an integrator circuit, such as integrator circuit 406 of FIG. 4, integrates the value of the sensor signal 502 during). Inset 514 provides a close-up of peaks 506a, and illustrates an integration interval 508 during which no reset signal is received at a reset circuit (such as reset circuit 408 of FIG. 4). Inset 514 also illustrates a maximum integration interval 510, which represents the time between the start of one stage of integration and the start of a second stage of integration. A maximum integration interval may be a fixed value (corresponding to, e.g., a fixed sampling frequency) or may vary. For example, as illustrated in FIG. 5, the maximum integration interval between the peaks in peaks 506a is shorter than the maximum integration interval between the peaks in peaks 506b. In some embodiments, the length of the maximum integration interval is inversely related to the magnitude of the sensor signal such that integration stages are spaced further apart in time as the magnitude of the sensor signal decreases. In CGM applications in which the sensor signal has a much higher magnitude at the initiation of monitoring, integrating the sensor signal over shorter intervals more often at the beginning of monitoring may prevent saturation of the integrator circuit because a reset signal is received before saturation is allowed to occur.

Figure 6:
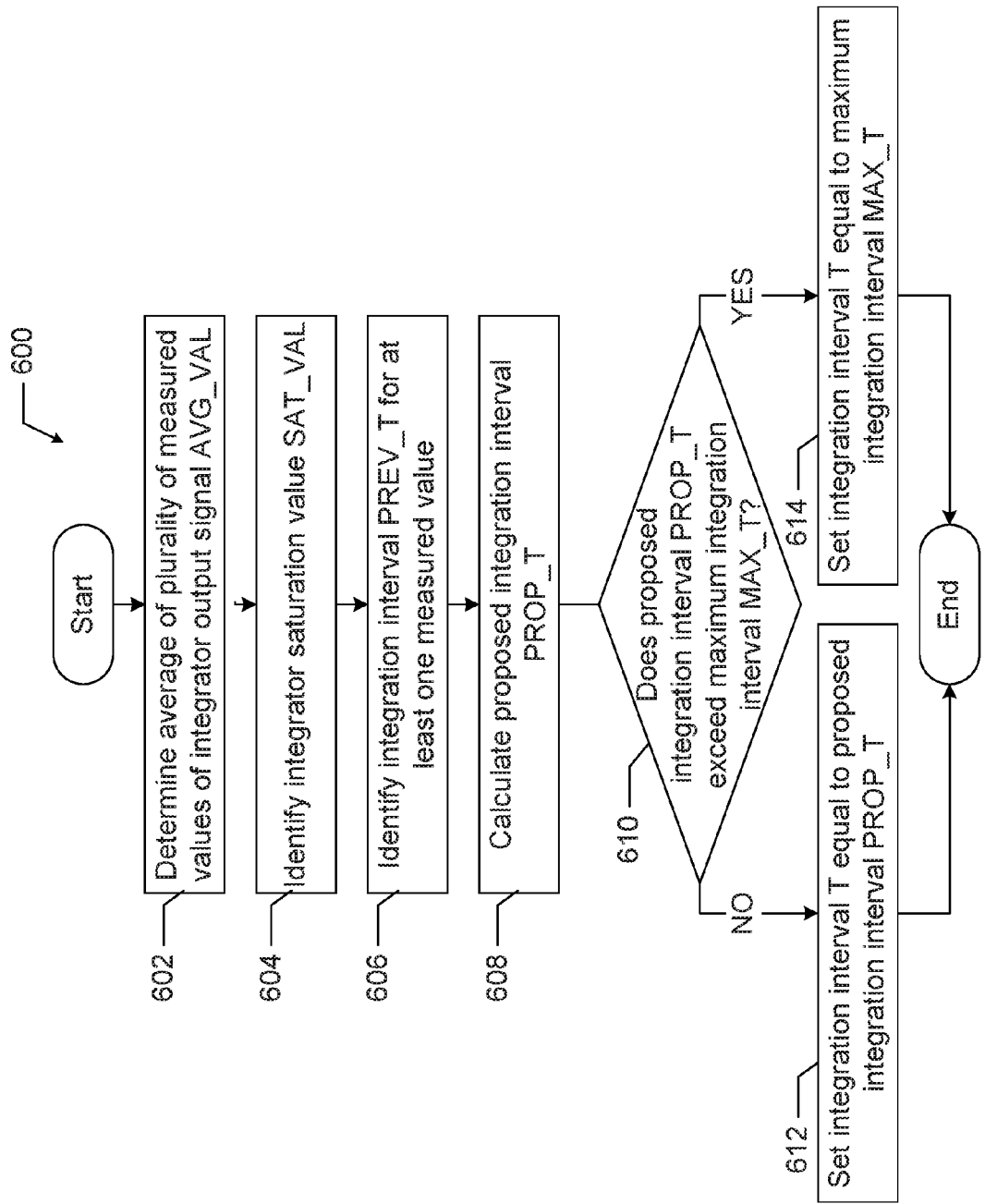
FIG. 6 is a flow diagram of a method of determining an integration interval, in accordance with various aspects.

An integration interval, such as integration interval 508, may be determined in any of a number of ways. FIG. 6 is a flow diagram 600 of a method of determining an integration interval, which may be performed by an electronics assembly (such as electronics assembly 100 of FIG. 1 or electronics assembly 400 of FIG. 4). In some embodiments, the method of flow diagram 600 may be used to determine the integration interval employed at block 308 of the signal processing method of FIG. 3. The method of flow diagram 600 determines the integration interval based at least in part on a saturation value of an integrator circuit included in an electronics assembly (such as integrator circuit 406 of FIG. 4), an average value of multiple measured values of an output signal of the integrator circuit, and at least one integration interval corresponding to a measured value of the output signal of the integrator circuit. For ease of illustration, flow diagram 600 will be described as performed by electronics assembly 400, but the method of flow diagram 600 may be performed by any suitably configured apparatus (such as a discrete component circuit using timing circuitry, a programmed processing device, or an application specific integrated circuit).

At block 602, electronics assembly 400 determines an average value AVG_VAL of multiple measured values of an integrator output signal (e.g., the voltage signal measured at output 410 of FIG. 4). For example, in some embodiments, processor circuit 414 calculates an average value of the last three integrator output measurements at block 602 and stores this value. At block 604, electronics assembly 400 identifies a saturation value SAT_VAL of integrator circuit 406. In some embodiments, a saturation value is a maximum value that may be output by integrator circuit 406. The saturation value may be a predetermined value based, for example, on a maximum output voltage of an amplifier included in integrator circuit 406 (such as OA 422) or another operating limitation of another component of electronics assembly 400. This saturation value may be stored in a memory and retrieved at block 604. At block 606, electronics assembly 400 identifies an integration interval PREV_T corresponding to at least one of the measured values averaged at block 602. In some embodiments, the integration interval identified at block 602 is the integration interval corresponding to most recently measured value of the integrator output signal. In some embodiments, the integration interval identified at block 602 is the average or maximum of two or more integration intervals corresponding to previously measured values of the integrator output signal.

At block 608, electronics assembly 400 calculates a proposed integration interval PROP_T. In some embodiments, the proposed integration interval calculated at block 608 is the longest interval that will not saturate the integrator circuit, assuming that the integrator output signal maintains a value equal to the average measured value AVG_VAL. In some such embodiments, the proposed integration interval is calculated in accordance with $$\text{PROP\_T} = \text{SAT\_VAL} \times \frac{\text{PREV\_T}}{\text{AVG\_VAL}} \quad (5)$$

The calculation represented by Eq. 5 may be especially advantageous when the integrator output signal changes slowly. At block 610, electronics assembly 400 determines whether the proposed integration interval PROP_T exceeds a maximum integration interval MAX_T. The maximum integration interval may be a predetermined value that may correspond, for example, to a maximum allowed interval between integrator output signal measurements by a processor circuit (such as processor circuit 414 of FIG. 4). If electronics assembly 400 determines that the proposed integration interval PROP_T does not exceed the maximum integration interval MAX_T, electronics assembly 400 proceeds to block 612 and sets the integration interval equal to the proposed integration interval PROP_T. If electronics assembly 400 determines at block 610 that the proposed integration interval PROP_T does exceed the maximum integration interval MAX_T, electronics assembly 400 proceeds to block 614 and sets the integration interval equal to the maximum integration interval MAX_T. The process then ends, and the integration of the next stage is performed over a time period equal in length to the determined integration interval.

To illustrate the advantages of some embodiments of the integrator systems, apparatuses and methods described herein over existing systems, an example is helpful. In an embodiment of sensor system 450 of FIG. 4 in which the sensor current signal averages 1 picoampere, the capacitance of capacitor 420 is less than or equal to 50 nanofarads and the integration interval is greater than or equal to 30 seconds, the integrator output value at the end of the integration interval (according to Eq. 3) is at least (1 picoampere)×(30 seconds)/(50 nanofarads)=600 microvolts, equivalent to a voltage-to-current ratio of 600 microvolts per picoampere or greater. Compared to existing systems utilizing transimpedance amplifiers (as discussed above), this voltage-to-current ratio is 1000 times greater and represents better noise performance. Additionally, since the integration interval need not remain constant as the magnitude of the sensor signal varies (e.g., as reflected in the integration interval determination method of FIG. 6), a smaller ADC may be used to achieve the same current sensitivity. For example, if a resolution of 5 picoamperes/level is desired when the sensor system is receiving a sensor signal approximately equal to 5 picoamperes, and the integration interval is assumed to be 30 seconds, the integrator output value at the end of the 30 second interval (according to Eq. 3) is (5 picoampere)×(30 seconds)/(50 nanofarads)=3 millivolts. To achieve the desired sensitivity with an integrator circuit that saturates at 3 volts, an ADC with a dynamic range of (3 volts)/(3 millivolts)=1000 levels may suffice, corresponding to a 10-bit ADC ($2^{10}$=1024). Compared to the 20-bit ADC required for some existing systems, a 10-bit ADC is much less expensive and consumes much less power. Thus, in some embodiments of the present disclosure, a processor circuit (such as processor circuit 414 of FIG. 4) may use the output of an ADC with a resolution of fewer than 18 bits to measure the integrator output signal.

Figure 7:
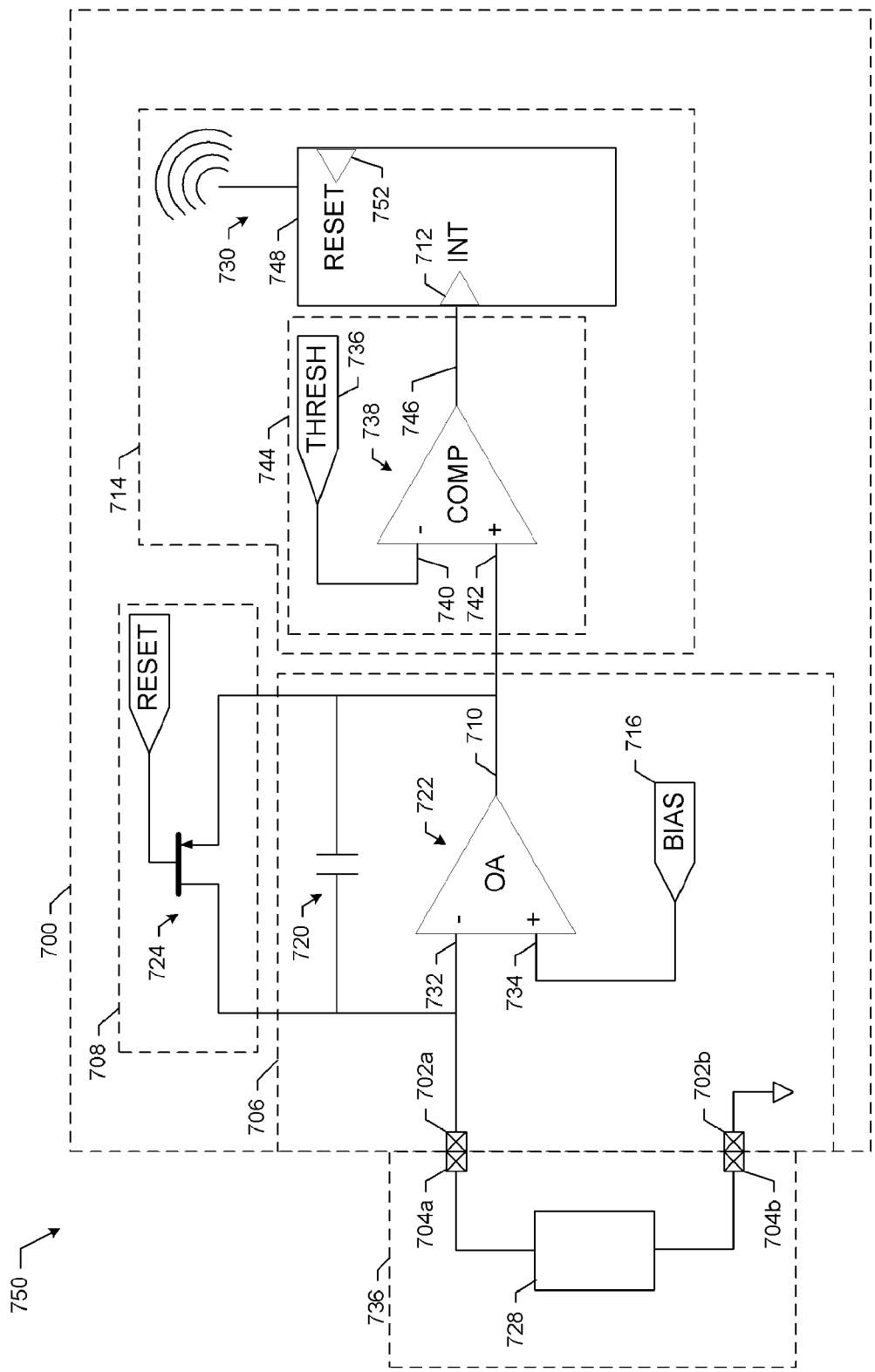
FIG. 7 is a schematic diagram of a sensor assembly and an electronics assembly including a comparator, in accordance with various aspects.

Another embodiment of electronics assembly 100 of FIG. 1 is now described. FIG. 7 is a schematic diagram of a sensor system 750 with a sensor assembly 736 and an electronics assembly 700 including a comparator, in accordance with various aspects. Electronics assembly 700 may be an embodiment of electronics assembly 100 of FIG. 1, and may be configured to perform the signal processing method of FIG. 3, as discussed above.

As shown in FIG. 7 and as discussed above with reference to FIG. 4, sensor assembly 736 includes a CGM or other type of sensor 728. Electronics assembly 700 includes an integrator circuit 706 (which may act as, e.g., integrator circuit 106 of FIG. 1) The components of electronics assembly 700 may be packaged in a hermetic housing (not shown) that is configured to be releasably coupled to the sensor assembly 736. Electronics assembly 700 includes sensor contacts 702a and 702b (which may act as, e.g., sensor contact 102 of FIG. 1) communicatively coupled with sensor contacts 704a and 704b of sensor assembly 436.

Electronics assembly 700 includes an integrator circuit 706 and a reset circuit 708. As shown, integrator circuit 706 is configured in a transimpedance integration configuration, and integrator circuit 706 and reset circuit 708 include many of the same components as were discussed above with reference to integrator circuit 406 and reset circuit 408 of FIG. 4, respectively. For clarity of presentation, a discussion of these components and their arrangements will not be repeated here. The integrator circuit 706 receives the sensor signal from sensor contacts 702a at input terminal 732 of operational amplifier (OA) 722 and converts the OA input signal into an OA output signal at OA output terminal 710. A bias voltage 716 is applied at the OA input terminal 734. In some embodiments, the relationship between the sensor current signal and the OA output voltage signal at output terminal 710 for the configuration of FIG. 7 may be given approximately by Eqs. 2-4, above.

As shown in FIG. 4, the OA output signal at OA output terminal 710 is sent to processor circuit 714 (which may act as, e.g., processor circuit 114 of FIG. 1). Processor circuit 714 includes a comparator circuit 744. Comparator circuit 744 is configured to compare the integrator output signal (received via OA output terminal 710) to a threshold value and provide an interrupt signal to processor 748 based on the comparison. Processor 748 may use the interrupt signal to provide a reset signal to reset circuit 708 (via reset output 752) in response to receiving an interrupt signal from comparator circuit 744. Processor circuit 414 may further include an antenna 730 and other wireless communication circuitry (not shown) to convey data about the processed sensor signal to other computing devices (not shown).

In the embodiment shown in FIG. 7, comparator circuit 744 includes comparator 738, which receives the integrator output signal from OA output terminal 710 at input terminal 742. Input terminal 740 of comparator 738 is coupled to a threshold voltage source 736. In some embodiments, the threshold voltage of threshold voltage source 736 is less than the saturation voltage of integrator circuit 706. The output terminal 746 of comparator 738 is connected to an interrupt input 712 of processor 748.

As discussed above with reference to FIG. 4, in some embodiments, some or all of the components of and around reset circuit 708 (which may include FET 724, capacitor 720 and OA 722) may be selected to have low leakage currents during use. In some embodiments, some or all of FET 724, capacitor 720 and OA 722 may be selected so that the magnitude of the total leakage current is less than approximately ten percent of the desired resolution of the integrator output signal. In some embodiments, some or all of FET 724, capacitor 720 and OA 722 may be selected so that the magnitude of the total leakage current is less than approximately five percent of the desired resolution of the integrator output signal. In some embodiments, some or all of FET 724, capacitor 720 and OA 722 may be selected so that the magnitude of the total leakage current is less than approximately one percent of the desired resolution of the integrator output signal.

Figure 8:
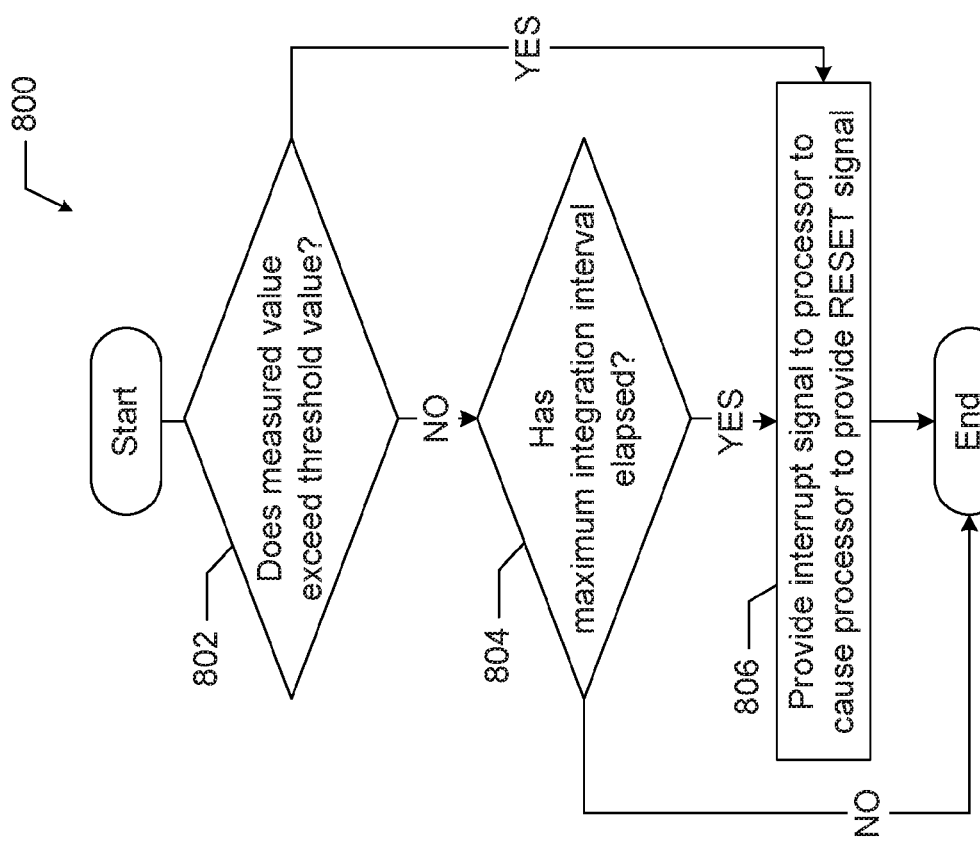
FIG. 8 is a flow diagram of a method for providing an interrupt signal, in accordance with various aspects.

In some embodiments, comparator circuit 744 is configured to provide an interrupt to processor 748 to trigger a reset signal. FIG. 8 is a flow diagram 800 of a method for providing an interrupt signal, which may be performed by an electronics assembly (such as electronics assembly 100 of FIG. 1 or electronics assembly 700 of FIG. 7). In some embodiments, the method of flow diagram 800 may be used to determine the integration interval employed at block 308 of the signal processing method of FIG. 3. For ease of illustration, flow diagram 800 will be described as performed by electronics assembly 700, but the method of flow diagram 800 may be performed by any suitably configured apparatus (such as a programmed processing device or application specific integrated circuit).

At block 802, electronics assembly 700 determines whether the value of the integrator output signal at input terminal 742 is greater than the value of the threshold voltage source 736. If no, electronics assembly 700 proceeds to block 804 and determines whether a maximum integration interval has elapsed. As discussed above with reference to block 610 of FIG. 6, the maximum integration interval of block 804 may be a predetermined value that may correspond, for example, to a maximum allowed interval between integrator output signal measurements. If electronics assembly 700 determines at block 804 that the maximum integration interval has not elapsed, the method may end. In some embodiments, this corresponds to the voltage at output terminal 746 of comparator 738 being a low value (e.g., approximately zero volts). If the value of the integrator output signal at input terminal 742 is determined to be greater than the value of the threshold voltage source 736 at block 802, or if the maximum integration interval is determined to have elapsed at block 804, electronics assembly 700 proceeds to block 806 and provides an interrupt signal to processor 748 to cause processor 748 to provide a reset signal to reset circuit 708. In some embodiments of block 806, the voltage at output terminal 746 of comparator 738 is a high value (e.g., approximately 5 volts). When the voltage at output terminal 746 goes high, processor 748 registers the receipt of an interrupt signal and may begin an preprogrammed interrupt response procedure, which may include providing a reset signal to reset circuit 708 in response to receiving the interrupt signal from comparator circuit 744. In some embodiments, processor 748 is programmed to stop providing the reset signal to reset circuit 708 at predetermined intervals (e.g., the maximum integration intervals discussed above with reference to FIGS. 5 and 6) and thus to initiate a next integration stage (not shown in FIG. 8).

Figure 9:
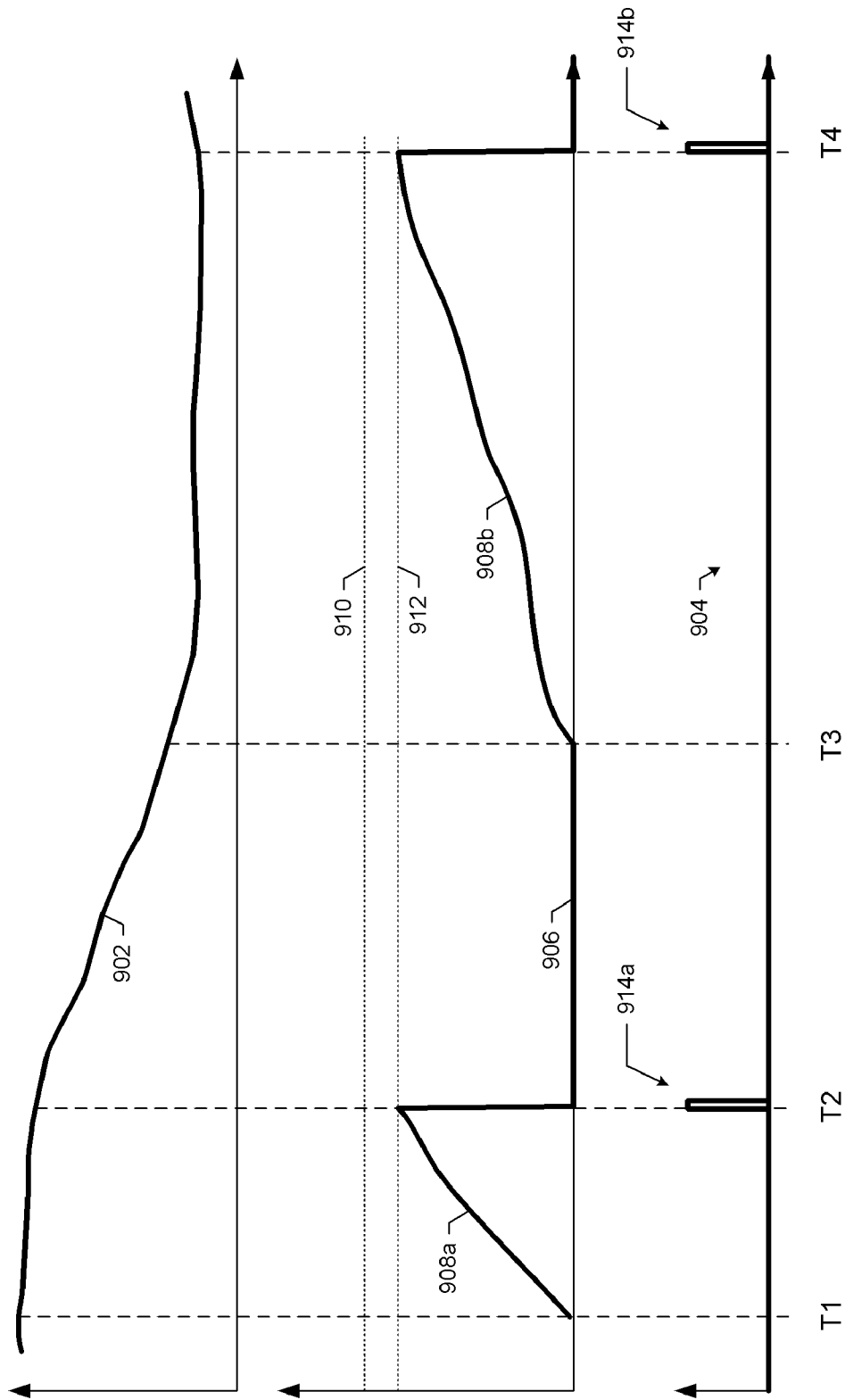
FIG. 9 illustrates an example sensor signal, corresponding integrator output signal, and corresponding interrupt signal that may be generated by an electronics assembly, such as the electronics assembly of FIG. 7, in accordance with various aspects.

FIG. 9 illustrates an example sensor signal 902, corresponding to integrator output signal 906, and corresponding interrupt signal 904 (with pulses 914a and 914b) that may be generated by an electronics assembly, such as electronics assembly 700 of FIG. 7. FIG. 9 illustrates two stages of integration: a first stage that begins at time T1 and a second stage that begins at time T3. The first integration interval extends from time T1 to time T2 and results in an integrator output signal portion 908a. When the magnitude of the integrator output signal reaches the comparator threshold value 912 (less than the integrator circuit saturation value of 910) at time T2, the comparator provides an interrupt signal pulse 914a to a processor, which triggers the resetting of the integrator output signal. The second integration interval extends from time T3 to time T4 and results in an integrator output signal portion 908b. When the magnitude of the integrator output signal reaches comparator threshold value 912 at time T4, the comparator provides an interrupt signal pulse 914b to a processor, which again triggers the resetting of the integrator output signal. 1

In some embodiments, processor 748 may determine a value of the integrator output signal (per block 306 of FIG. 3) by retrieving the known threshold value from a memory or by measuring the threshold value from threshold voltage source 736. Because comparator circuit 744 provides an interrupt signal when the value of the integrator output signal reaches the known threshold value, processor 748 may determine an average value of the sensor signal over the integration interval in response to receiving the interrupt signal by determining an elapsed time between the first time and a time at which the interrupt signal is received at the processor (e.g., the length of the integration interval). For example, in accordance with Eq. 3 above, the average sensor current signal $I_S$ may be calculated as $$I_S = \frac{THRESH \times C}{T}, \qquad (6)$$

where THRESH is the value of threshold voltage source 736, C is the capacitance of capacitor 720, and T is the length of the integration interval.

Figure 10:
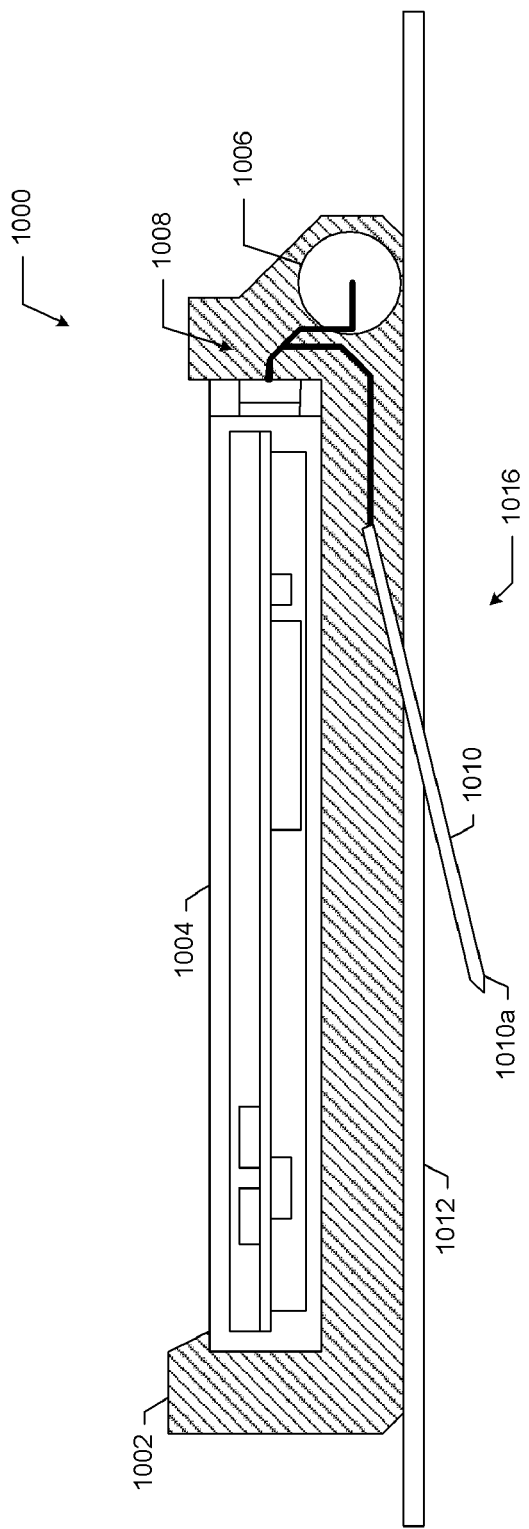
FIG. 10 is a plan view of an analyte sensor system that may include any of the sensor and/or electronics assemblies described herein, in accordance with various aspects.

FIG. 10 is a plan view of an analyte sensor system 1000 that may include any of the sensor and/or electronics assemblies described herein (such as those described with reference to FIGS. 1, 4 and 7). A sensor assembly 1016 includes an analyte sensor 1010 configured to, when sensor assembly 1016 is positioned against a body, produce a sensor signal that is representative of a level of an analyte in the body. Sensor assembly 1016 may include, for example, any of the sensor assemblies described herein. In some embodiments, analyte sensor 1010 includes a sharp distal end 1010a configured to be positioned within the body when the sensor assembly 1016 is positioned against the body. In some embodiments, analyte sensor 1010 includes a continuous glucose monitor.

A housing portion 1002 is coupled to sensor assembly 1016. An adhesive pad 1012 is disposed between housing portion 1002 and the body when in use, and a battery 1006 is disposed within housing portion 1002. In some embodiments, battery 1006 is non-rechargeable. In some embodiments, battery 1006 is molded into housing portion 1002, and cannot be removed. Battery 1006 may, for example, include one or more Li—MnO2 and/or silver oxide batteries. In some embodiments, housing portion 1002 is disposable when battery 1006 can no longer provide adequate power. In some embodiments, battery 1006 is a rechargeable battery, or includes a rechargeable battery.

Electronics assembly 1004 may take the form of any of the electronics assemblies described herein, such as electronics assembly 100 of FIG. 1, electronics assembly 400 of FIG. 4, and electronics assembly 700 of FIG. 7. Electronics assembly 1004 may be configured to perform any of the methods described herein, such as the method of FIG. 3, the method of FIG. 5, and the method of FIG. 8. For example, in some embodiments, electronics assembly 1004 includes battery contacts 1008 configured to electrically couple battery 1006 to electronics assembly 1004 when electronics assembly 1004 is coupled to sensor assembly 1016. Electronics assembly 1004 may also include a sensor contact configured to receive a sensor signal from analyte sensor 1010, an integrator circuit coupled to the sensor contact and configured to provide an integrator output signal representative of the sensor signal integrated over time, a reset circuit coupled to the integrator circuit and configured to reset the integrator output signal in response to a reset signal, and a processor coupled to the integrator circuit and the reset circuit. The processor may be configured to determine a value of the integrator output signal and to provide the reset signal to the reset circuit when an integration interval has elapsed from the first time, the integration interval based at least in part on the integrator output signal.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. An electronics assembly comprising:
   a contact configured to receive a sensor signal from an analyte sensor assembly in contact with a body, the sensor signal representative of a level of an analyte in the body;
   an integrator circuit coupled to the contact and configured to provide an integrator output signal representative of the sensor signal integrated from a first time to a second time;
   a reset circuit coupled to the integrator circuit and configured to reset the integrator output signal in response to a reset signal; and
   a processor circuit coupled to the integrator circuit and the reset circuit, the processor circuit configured to determine a value of the integrator output signal and to provide the reset signal to the reset circuit when an integration interval has elapsed from the first time, the integration interval based at least in part on the integrator output signal.

2. The electronics assembly of claim 1, wherein the analyte sensor assembly includes a continuous glucose monitor configured to generate the sensor signal.

3. The electronics assembly of claim 1, wherein the analyte sensor assembly includes an electrochemical blood glucose monitor or an optical blood glucose monitor configured to generate the sensor signal.

4. The electronics assembly of claim 1, wherein the integrator circuit comprises an amplifier configured to receive the sensor signal at an amplifier input and to provide an amplified sensor signal at an amplifier output, the amplified sensor signal having a voltage dependent on a current of the sensor signal at the amplifier input.

5. The electronics assembly of claim 4, wherein the integrator circuit further comprises a capacitor coupled to the amplifier input and to the amplifier output.

6. The electronics assembly of claim 5, wherein the reset circuit comprises a switch configured to close in response to receiving the reset signal at the reset circuit.

7. The electronics assembly of claim 4, wherein the integrator circuit comprises an analog-to-digital converter (ADC) having an ADC input coupled to the amplifier output and an ADC output coupled to the integrator output.

8. The electronics assembly of claim 7, wherein the ADC has a resolution of less than 18 bits.

9. The electronics assembly of claim 1, wherein the processor circuit is further configured to determine the integration interval based at least in part on a measurement of the integrator output signal.

10. The electronics assembly of claim 1, wherein the processor circuit comprises a comparator circuit coupled to the integrator circuit and configured to:
    compare the integrator output signal to a threshold value; and
    provide an interrupt signal to a processor of the processor circuit based on the comparison,
    wherein the processor is configured to provide the reset signal to the reset circuit in response to receiving the interrupt signal from the comparator circuit.

11. The electronics assembly of claim 10, wherein the threshold value is less than a saturation value of an amplifier included in the integrator circuit.

12. The electronics assembly of claim 10, wherein the processor circuit is further configured to determine an average value of the sensor signal between the first and second times in response to receiving the interrupt signal by determining an elapsed time between the first time and a time at which the interrupt signal is received at the processor.

* * * * *